United States Patent
Sofia et al.

(10) Patent No.: US 10,485,428 B2
(45) Date of Patent: Nov. 26, 2019

(54) THERMOMETER WITH WIRELESS FUNCTIONALITY

(71) Applicant: Helen of Troy Limited, St. Michael (BB)

(72) Inventors: Katherine Sofia, Wakefield, MA (US); Leslie Juhng, Cliffside Park, NJ (US); Lynne Hammell, Boston, MA (US); James Gorsich, Los Angeles, CA (US)

(73) Assignee: Helen of Troy Limited, St. Michael (BB)

( * ) Notice: Subject to any disclaimer, the term of this patent is extended or adjusted under 35 U.S.C. 154(b) by 712 days.

(21) Appl. No.: 14/860,818

(22) Filed: Sep. 22, 2015

(65) Prior Publication Data

US 2016/0081559 A1    Mar. 24, 2016

Related U.S. Application Data

(60) Provisional application No. 62/053,579, filed on Sep. 22, 2014.

(51) Int. Cl.
*A61B 5/00* (2006.01)
*A61B 5/01* (2006.01)
(Continued)

(52) U.S. Cl.
CPC .............. *A61B 5/01* (2013.01); *A61B 5/0008* (2013.01); *A61B 5/72* (2013.01); *A61B 5/742* (2013.01);
(Continued)

(58) Field of Classification Search
CPC ......... A61B 5/01; A61B 5/015; A61B 5/0008; A61B 5/72; A61B 5/742; G01K 5/22;
(Continued)

(56) References Cited

U.S. PATENT DOCUMENTS

| | | |
|---|---|---|
| 4,986,669 A | 1/1991 | Yamaguchi |
| 5,181,521 A | 1/1993 | Lemelson |

(Continued)

FOREIGN PATENT DOCUMENTS

| | | |
|---|---|---|
| CN | 1971224 | 5/2007 |
| CN | 200948139 | 9/2007 |

(Continued)

OTHER PUBLICATIONS

International Search Report and Written Opinion dated Apr. 14, 2016 in International Application No. PCT/IB2015/002066.

(Continued)

*Primary Examiner* — Max F Hindenburg
(74) *Attorney, Agent, or Firm* — Rankin, Hill & Clark LLP

(57) ABSTRACT

A thermometer includes a temperature sensor, a computation circuit, and a wireless communications circuit. The computation circuit includes a memory and a processor, with the memory storing program code to perform the various functions of the thermometer, including computing a temperature of the patient based upon the one or more readings, and to store this temperature in the memory. The processor may also store the time at which the readings were obtained and associate it with the stored temperature. The wireless communications circuit and the computation circuit are used to establish a wireless communications link with an external device to provide temperature values stored in the memory to the external device. The associated time of the stored temperature may also be communicated to the external device. The external device can be used to view the temperature readings and to configure the thermometer.

36 Claims, 6 Drawing Sheets

(51) Int. Cl.
*G01K 13/00* (2006.01)
*G01K 1/02* (2006.01)

(52) U.S. Cl.
CPC .............. *A61B 5/746* (2013.01); *G01K 1/024* (2013.01); *G01K 13/002* (2013.01)

(58) Field of Classification Search
CPC ........ G01K 5/24; G01K 13/00; G01K 13/002; G01K 13/004
See application file for complete search history.

(56) References Cited

U.S. PATENT DOCUMENTS

| | | | |
|---|---|---|---|
| 6,929,611 B2 | 8/2005 | Koch | |
| 7,854,550 B2 | 12/2010 | Chan et al. | |
| 7,883,463 B2 | 2/2011 | Sattler et al. | |
| 8,042,997 B2 | 10/2011 | Lyndon et al. | |
| 8,808,178 B2* | 8/2014 | Lane | A61B 5/01 600/300 |
| 8,816,875 B2* | 8/2014 | Hiramatsu | G01K 13/002 340/588 |
| 8,827,552 B2* | 9/2014 | Tseng | G01K 13/002 374/100 |
| 8,974,115 B2 | 3/2015 | Segal et al. | |
| 9,204,806 B2* | 12/2015 | Stivoric | G06F 19/3418 |
| 9,445,726 B2* | 9/2016 | Toriumi | G01K 13/002 |
| 9,592,033 B2* | 3/2017 | Toriumi | A61B 5/746 |
| 9,593,985 B2 | 3/2017 | Segal et al. | |
| 2007/0116089 A1 | 5/2007 | Bisch et al. | |
| 2007/0161921 A1 | 7/2007 | Rausch | |
| 2011/0084132 A1 | 4/2011 | Tofighbakhsh | |
| 2015/0120236 A1 | 4/2015 | Bhoot | |
| 2016/0026768 A1 | 1/2016 | Singh et al. | |

FOREIGN PATENT DOCUMENTS

| | | |
|---|---|---|
| CN | 201617812 | 11/2010 |
| CN | 202477664 | 10/2012 |
| CN | 103604511 | 2/2014 |
| CN | 103961070 | 8/2014 |
| EP | 2060228 A1 | 5/2009 |
| GB | 2408105 | 5/2005 |
| JP | 2009031264 | 2/2009 |
| JP | 2011067292 | 4/2011 |
| JP | 2013140529 | 7/2013 |

OTHER PUBLICATIONS

Supplementary EP Search Report filed in EP 15844285 dated May 3, 2018.
Chinese Office action dated May 24, 2019.

* cited by examiner

THERMOMETER WITH WIRELESS FUNCTIONALITY

CROSS-REFERENCE TO RELATED APPLICATIONS

This application claims the benefit of U.S. Provisional Application No. 62/053,579, filed Sep. 22, 2014, the contents of which are incorporated herein by reference.

BACKGROUND OF THE INVENTION

1. Field of the Invention

The present invention generally relates to thermometry. In particular, various embodiments relate to a medical thermometer that includes a wireless capability to provide temperature readings to another device.

2. Description of the Related Art

Various types of thermometers are known, including both contact and non-contact thermometers. Contact-type thermometers generally rely upon conduction between the patient and a sensor component, which may include a thermistor or the like, to cause heating of the sensor component that is then detected and converted to a corresponding temperature of the patient. Non-contact thermometers rely upon radiation read from a specific location in or on the patient, which is detected by a radiation-based sensor, such as a thermopile, and converted into a corresponding patient temperature. Various algorithms are known that use the output of the specific type of sensor employed, and, sometimes, the ambient temperature, to a generate a corresponding type of temperature of the patient, such as an oral temperature, tympanic temperature, core temperature or the like.

Regardless of the underlying detection and conversion technology that is used, in each case the thermometer requires a display to present the computed temperature to the user. This display adds extra expense to the thermometer and requires additional space in the thermometer housing.

SUMMARY OF THE INVENTION

In view of the foregoing, there exists a need for a thermometer that can communicate temperature readings to an external device, thus relieving the need for the thermometer to have a display, along with any related components and associated costs.

According to one embodiment, a thermometer includes a sensor for obtaining a temperature reading from a patient and generating a corresponding sensor signal. A computation circuit of the thermometer is coupled to the sensor and configured to compute a corresponding temperature of the patient based upon one or more readings obtained from the sensor. The computation circuit includes a memory and a processor. The memory includes program code that is executable by the processor to cause the processor to perform the various functions of the thermometer, including computing a temperature of the patient based upon the one or more readings, and to store this temperature in the memory. The processor may also store the time at which the readings were obtained and associate it with the stored temperature. The thermometer also includes a wireless communications circuit coupled to the computation circuit. The wireless communications circuit and the computation circuit are collectively configured to establish a wireless communications link with an external device to provide temperature values stored in the memory to the external device. The associated time of the stored temperature, as well as other information, may also be communicated to the external device.

BRIEF DESCRIPTION OF THE DRAWINGS

The various aspects and embodiments disclosed herein will be better understood when read in conjunction with the appended drawings, wherein like reference numerals refer to like components. For the purposes of illustrating aspects of the present invention, there are shown in the drawings certain preferred embodiments. It should be understood, however, that the invention is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings.

DETAILED DESCRIPTION OF THE PREFERRED EMBODIMENTS

Figure 1:
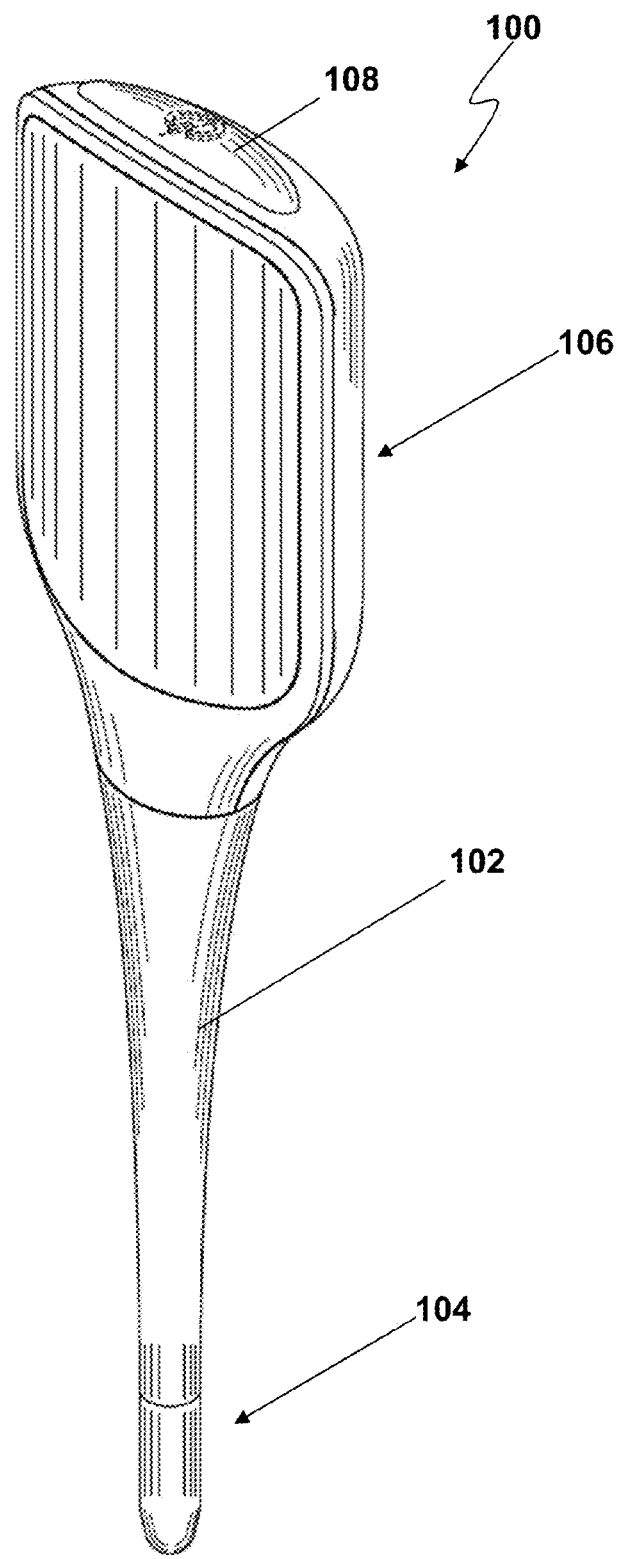
FIG. 1 is a perspective view of an embodiment thermometer.

FIG. 1 is a perspective view of an embodiment thermometer 100. Although a contact thermometer is shown, it will be appreciated that the present description is also applicable to non-contact thermometers. The thermometer 100 includes a body 102 that contains a sensor portion 104 and an electronics portion 106. The body 102 may be configured as a stick thermometer, as shown. However, the body 102 may also be configured for other types of thermometers, such as forehead thermometers, axillary thermometers, tympanic thermometers and the like. Non-limiting examples of thermometer types and sensor configurations that can be used for the thermometer 100 include U.S. Pat. No. 7,785,266, entitled "MEDICAL THERMOMETER FOR DETERMINING BODY CORE TEMPERATURE," the contents of which are incorporated herein by reference; United States Patent Publication No. 2011/0137201, entitled "ORAL THERMOMETER WITH CURVED PROBE," the contents of which are incorporated herein by reference; and United States Patent Publication No. 2011/0228811, entitled "NON-CONTACT MEDICAL THERMOMETER WITH STRAY RADIATION SHIELDING," the contents of which are incorporated herein by reference. It will be appreciated that other sensor types and configurations are possible, however.

The sensor portion 104 includes any suitable electronics and materials to obtain temperature readings from a patient, and may include contact and/or non-contact components. The sensor portion 104 is connected to the electronics portion 106 and provides a signal to the electronics portion 106 corresponding to the readings that the electronics portion 106 then converts to a corresponding temperature value of the patient. The temperature value may be any suitable value, including the actual temperature obtained from the sensor portion 104, or a converted temperature based upon the reading or readings from sensor portion 104. A converted temperature can indicate, for example, the core temperature of the person, an oral temperature of the person, a tympanic temperature of the person, or any other suitable temperature of the patient. Algorithms for converting one or more temperature readings from a sensor portion 104 into such converted temperature values are known (including, but not limited to, the example described in the above-indicated U.S. patent documents), and any such converted temperature value and related algorithm may be employed by the electronics portion 106. Alternatively, the electronics portion 106 may provide raw data from the sensor portion 104 to an external device 10 (which raw data may include temperature readings of the patient or data representative thereof and, optionally, the ambient environment, the temperature of or within sensor portion 104, or any other desirable information), and the external device 10 then performs the conversion. The body 102 may also include one or more buttons 108 or the like, which can be used as an input device for the user to turn the thermometer 100 on and off, to select certain functions or modes of the thermometer 100 (e.g., type of temperature conversion to be performed), indicate a patient being checked, etc. In preferred embodiments, the body 102 does not include a screen for presenting numerical temperature data to a user, although in other embodiments a screen can be provided and used to interface with a user.

Figure 2A:
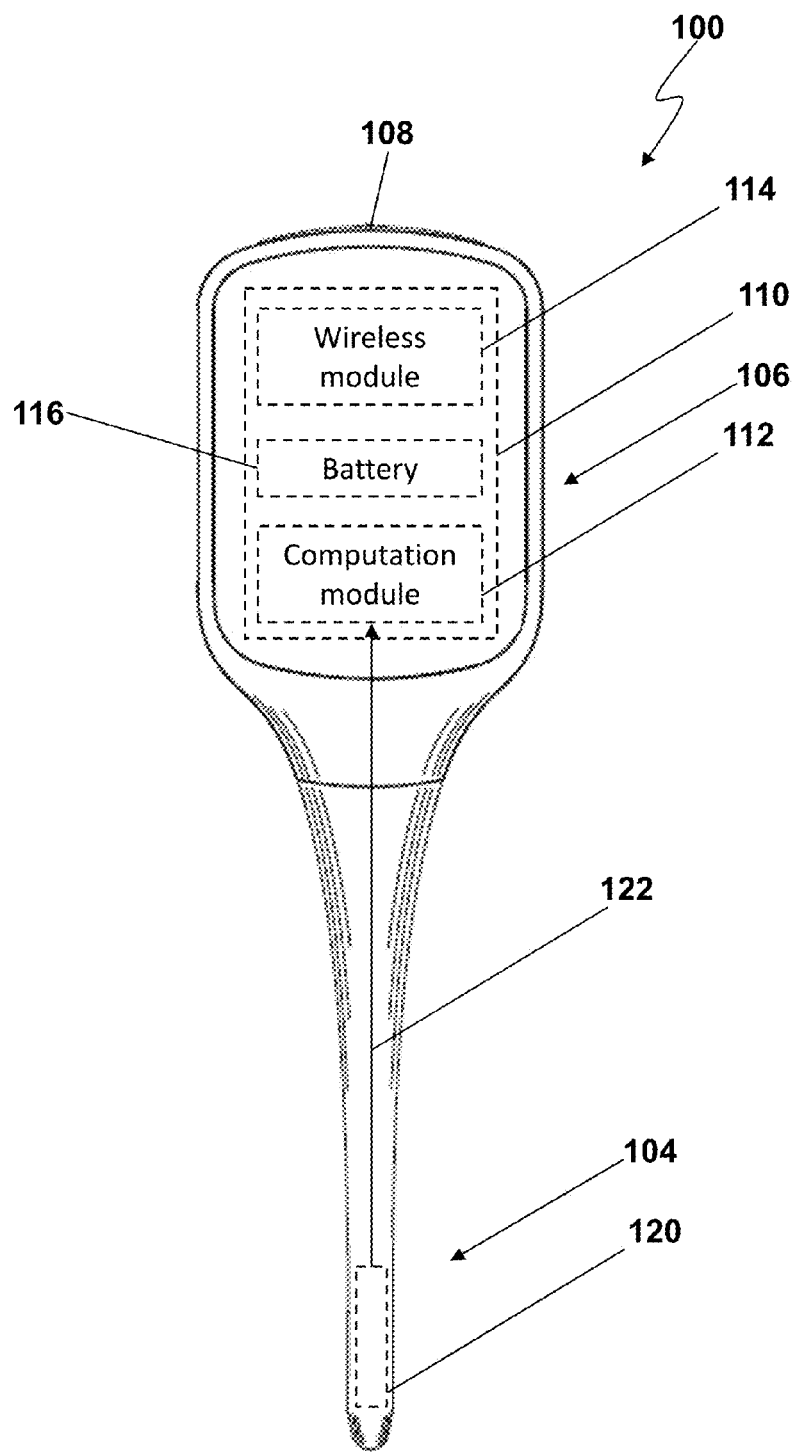
FIG. 2A illustrates various internal components of the thermometer shown in FIG. 1.

As shown in FIG. 2A, an electronics assembly 110 is disposed within the electronics portion 106 and is electrically connected to both a sensor assembly 120 disposed within the sensor portion 104 and to the button or buttons 108. The sensor assembly 120 includes any electronics and related components needed to obtain physical measurements of the temperature of a patient and may include, for example, one or more of: (1) a target sensor, which obtains a temperature measurement from the patient; (2) an ambient temperature sensor to measure the temperature around the patient, and (3) a device temperature sensor that measures the temperature of the thermometer 100 itself, and more particularly, of the target sensor. Data related to readings from the one or more sensors is then placed on a signal line or lines 122 to be transmitted to the electronics assembly 110.

Figure 2B:
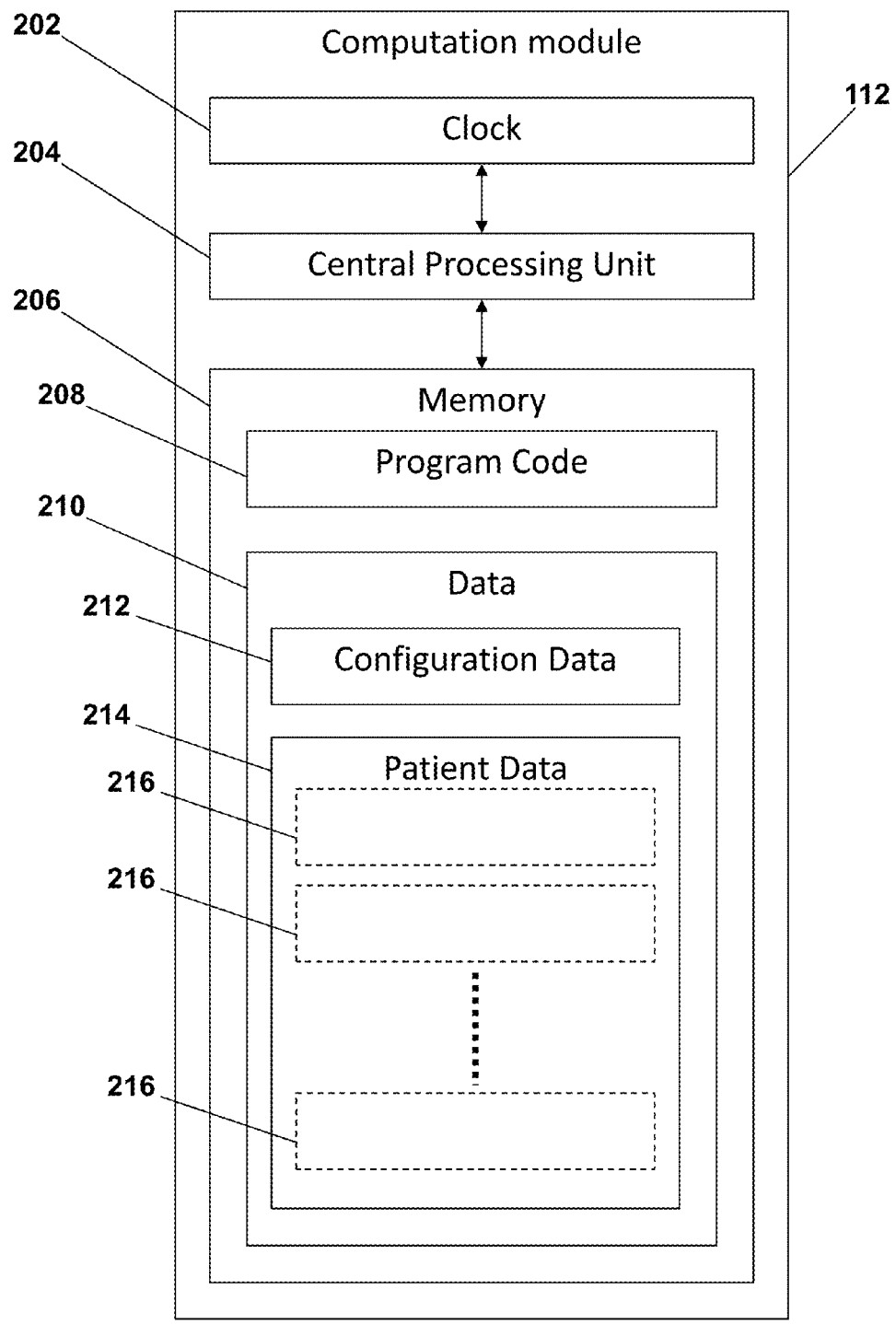
FIG. 2B illustrates various aspects of an embodiment computation module depicted in FIG. 2A.

The electronics assembly 110 includes a computation module 112 that receives sensor signals from the signal line or lines 122 and converts these sensor signals into a corresponding converted temperature of the patient. This conversion is preferably based upon the desired temperature conversion type (e.g., oral, rectal, axillary, tympanic, etc.) and the type of target sensor used in the sensor package 120 (thermistor, thermopile, thermocouple, etc.). The computation may also be based upon the ambient temperature. The computations from raw sensor data to a converted patient temperature may be based upon any known or suitable algorithm, or may be based upon a lookup table. Referring not to FIG. 2B, the computation module 112 preferably includes a processor 204 coupled to memory 206 and to a clock 202 that tracks the date, time or, preferably, both. It will be appreciated that this arrangement can be provided by, for example, a system on a chip that includes all of these desired components in a single package. The memory 206 includes program code 208 executable by the processor 204 to cause the processor 204 to perform various functions, including reading the sensor signals from the sensor assembly 120 and converting these signals into a corresponding temperature, reading the clock 202 to establish a date and time that a temperature measurement was made, and storing temperature measurements in the memory 206 in a data portion 210 of memory 206. The memory 206 thus preferably includes both volatile and readable/writable non-volatile memory, as known in the art.

The data portion 210 can include, for example, configuration data 212, which is used by the processor 204 to configure the thermometer 100. For example, the configuration data 212 can indicate the type of temperature conversion to perform (oral, tympanic, rectal, axillary, core, etc., or none—e.g., the actual temperature measured by the sensor assembly 120). The configuration data 212 can also store calibration data for the sensor assembly 120 to assist in the temperature conversion, can hold patient name or other identifying characteristics, and store any other data suitable for managing the functionality of thermometer 100.

The data portion 210 can also include a table of patient data 214. Each entry 216 in table 214 can correspond to a measurement made of a patient, and may include, for example, one or more of: (1) the temperature of the patient; (2) what the temperature corresponds to, such as, core, tympanic, oral, rectal, actual, etc. (as obtained from the current configuration data 212); (3) the time the measurement was made (as obtained from clock 202); (4) an identifier of the patient (as obtained, for example, from the current configuration data 212); (5) the underlying raw sensor data obtained from sensor assembly 120, and (6) any other suitable information.

In some embodiments the computation module 112 is electrically coupled to the one or more buttons 108 to allow the user to change the functionality of the thermometer 100, which may be reflected in the configuration data 212. For example, the computation module 112 can be programmed to interpret holding the button 108 down for three seconds or more as a power-off or power-on indicator, and enter into a low-power quiescent state or higher-power active state accordingly. Relatively rapid double-clicks of the button 108 may be interpreted, for example, as an indication to cycle into another mode of the thermometer, such as from oral to tympanic, tympanic to axillary, axillary to rectal, rectal to oral, etc., which is then stored in the configuration data 212 and used when performing temperature conversions. Triple-clicking may indicate, for example, toggling between degrees Celsius and degrees Fahrenheit, which may also be stored in the configuration data 212 and used for temperature conversions. Other input schemas are also possible, including using sliding or position-sensitive buttons or knobs to select a mode, using multiple buttons for respective functions, etc. In other embodiments, however, the thermometer 100 has no buttons, knobs, sliders or the like 108 and thus is free of visible user input devices.

For embodiments with user input devices, the thermometer 100 can include buttons, switches or sliders 108 that are assigned to indicate different patients whose temperatures are being taken, and which may be stored in the configuration data 212 as needed. In some embodiments, when taking a temperature, the user can first move a button, slider or the like 108 to a position or state that indicates the patient whose temperature is being taken. In other embodiments, the thermometer 100 can use signal information obtained from a wireless module 114, such as WiFi signals, near field communication (NFC) signals or the like, to estimate a position of the thermometer 100 and associate the position of the thermometer 100 with a patient, analogous or equivalent to a patient selector or identification button 108. In particular, the thermometer 100 can measure the strength of one or more wireless signals and associate these strengths with a physical location of the thermometer 100, which, in turn, can be associated with a patient. For example, the thermometer 100 may measure the signal strength of a WiFi router or the like in a home; as the thermometer 100 is moved from room to room, the router WiFi signal strength will vary accordingly. Based upon these variations, the thermometer 100 may associate the signal WiFi strength with a corresponding patient. Hence, this wireless signal strength information can be stored in the memory 206 and associated with a specific patient. Thereafter, the computation module 112 associates each temperature taken with the determined patient based on, for example, the measured WiFi signal strength, together with the date/time and temperature type, and stores this information into the corresponding memory entry 216.

The electronics assembly 110 also includes the wireless module 114 which is in communications with, and can be controlled by, the computation module 112. The wireless module 114 may be any suitable wireless system as known in the art to establish communications with another device, such as, but not limited to, Bluetooth (IEEE 802.15.1), UWB (IEEE 802.15.3), ZigBee (IEEE 802.15.4), and Wi-Fi (IEEE 802.11a/b/g). The computation module 112 can provide data to the wireless module 114, which the wireless module 114 can then wirelessly forward to another device; in this manner, the thermometer 100 can share temperature readings and related data with another wireless device that has, for example, been paired with the wireless module 114. The wireless module 114 may also receive data from another wireless device and provide this data to the computation module 112; in this manner, another device may be used to control the functionality of the thermometer 100, and corresponding updates can then be made to the configuration data 212 as desired.

Finally, the electronics assembly 110 includes a battery 116 that is used to power the computation module 112 and the wireless module 114. The battery 116 may be rechargeable, or may be disposable. A door or the like in the body 102 may provide access to a compartment within which the battery 116 is stored so as to allow easy replacement of battery 116.

Figure 3:
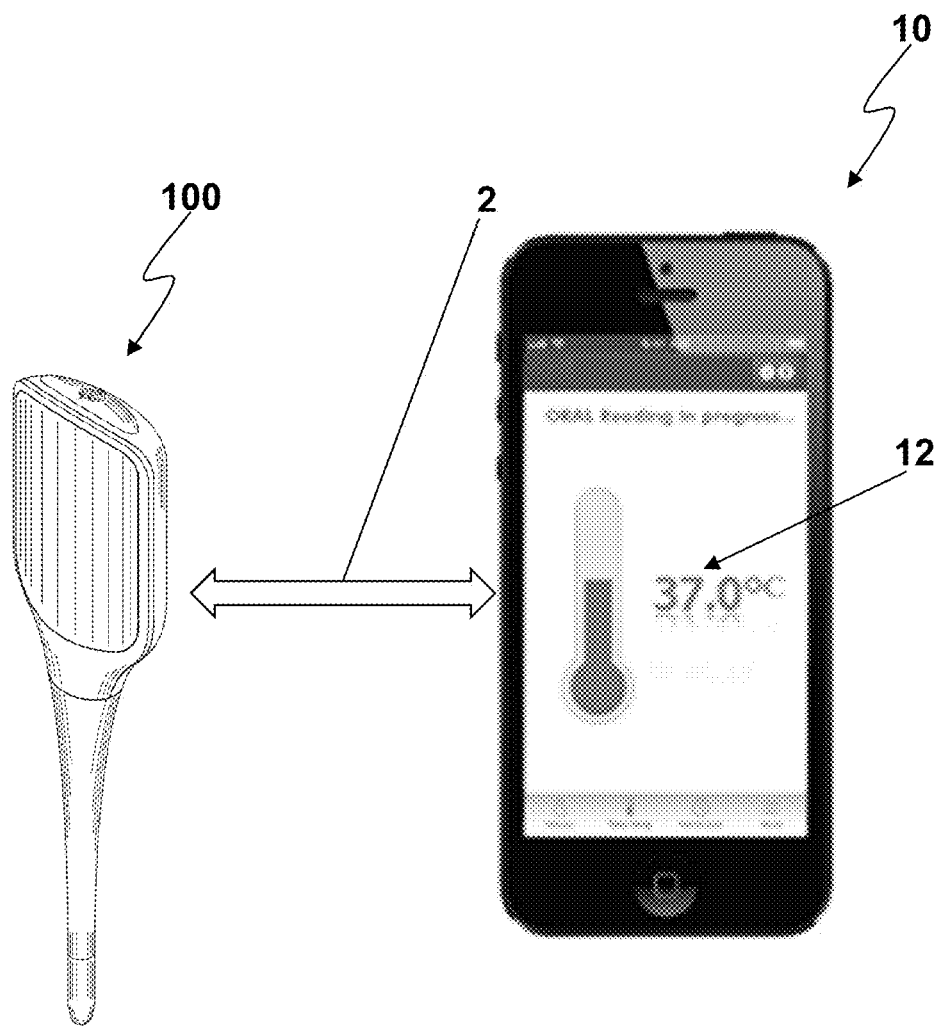
FIG. 3 illustrates the thermometer of FIG. 1 communicating with an external computing device.
Figure 4:
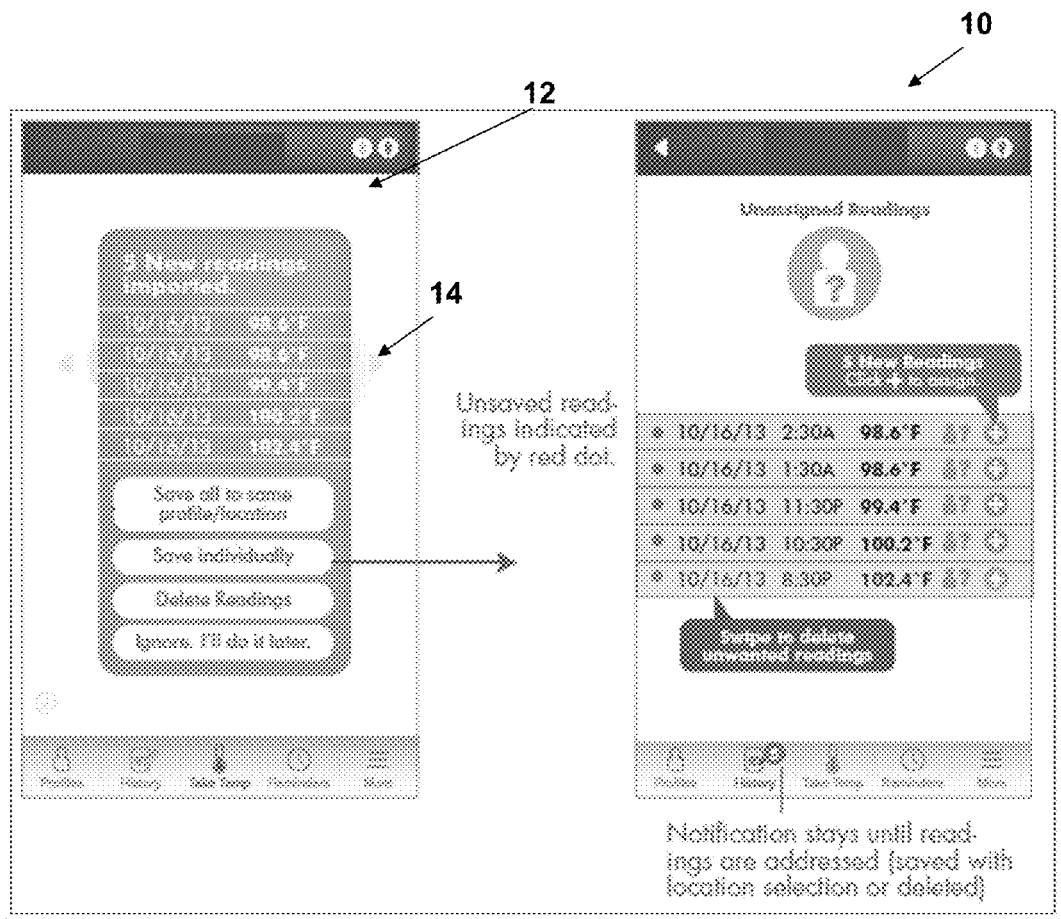
FIG. 4 illustrates an aspect of a user interface for the external computing device shown in FIG. 3.

As illustrated in FIGS. 3 and 4, using the electronics assembly 110, and in particular the wireless module 114, the thermometer 100 may communicate with another computing device 10, such as a mobile phone, a personal computer or the like, by establishing a wireless communications link 2 between the devices 10, 100. The computing device 10 includes a processing circuit having a processor, memory and a related program executable by the processor to cause device 10 to establish communications with the thermometer 100 and to support various functions in relation to the thermometer 100 via a user interface 14 present on the display 12. This program may be, for example, an application or "app" that a user of the computing device 10 may download and install into the computing device 10 for subsequent execution, as known in the art, to provide the functionality of the external device 10 in relation to the thermometer 100 as described herein. For example, the program on the computing device 10 can be used to pair the thermometer 100 with the computing device 10, using suitable protocols, such as Bluetooth. Thereafter, when in wireless proximity to the external computing device 10, the thermometer 100 will automatically establish the communications link 2 and thus communicate with the external device 10.

In certain embodiments, the thermometer 100 automatically senses an increase in temperature of the sensor portion 104 when a temperature is being taken and begins collecting and processing temperature data in response thereto. When the thermometer 100 is used to take the temperature of a patient, the thermometer 100 uses the communications link 2, if present, to communicate with the program on the computing device 10 and send the resultant temperature measurement and related data contemporaneously to the external computing device 10, and can also receive commands from the computing device 10. The computing device 10 can display this temperature and related data on its display screen 12 and also present a user interface 14 to control operational aspects of the thermometer 100, such as instructing the thermometer 100 to take another temperature, change the patient indicator, etc. In preferred embodiments, the thermometer 100 sends a stream of temperature measurement data to the computing device 10. The computing device 10 uses this data to present a real-time progress report on the display screen 12 of a temperature-taking process being performed by the thermometer. For example, the display screen 12 may show the temperature rising on the screen 12 in a visual manner, with numbers, or both, so that the user can see that a measurement is in progress. The temperature shown may be, for example, a raw or converted temperature measurement obtained from the sensor assembly 120. When the measurement is complete, the computing device 10 can then display the final converted temperature, together with the type of conversion, on the screen 12. Also, when the measurement process is complete, the thermometer 100 may provide an audio and/or visual signal to the user. Changes to the thermometer configuration as received from the communications link 2 can be reflected in the configuration data 212.

When the thermometer 100 detects that no communications link 2 is present when a temperature measurement process is initiated, the thermometer 100 preferably stores the temperature reading and its related data in the memory of the computation module 112. The thermometer 100 can provide an audio and/or visual indicator to the user to indicate that the temperature measurement is in process, and when the temperature measurement process has been completed. When a link 2 is finally established, any new measurement data 216 can be provided to the computing device 10 for presentation in the display 12.

Figure 5:
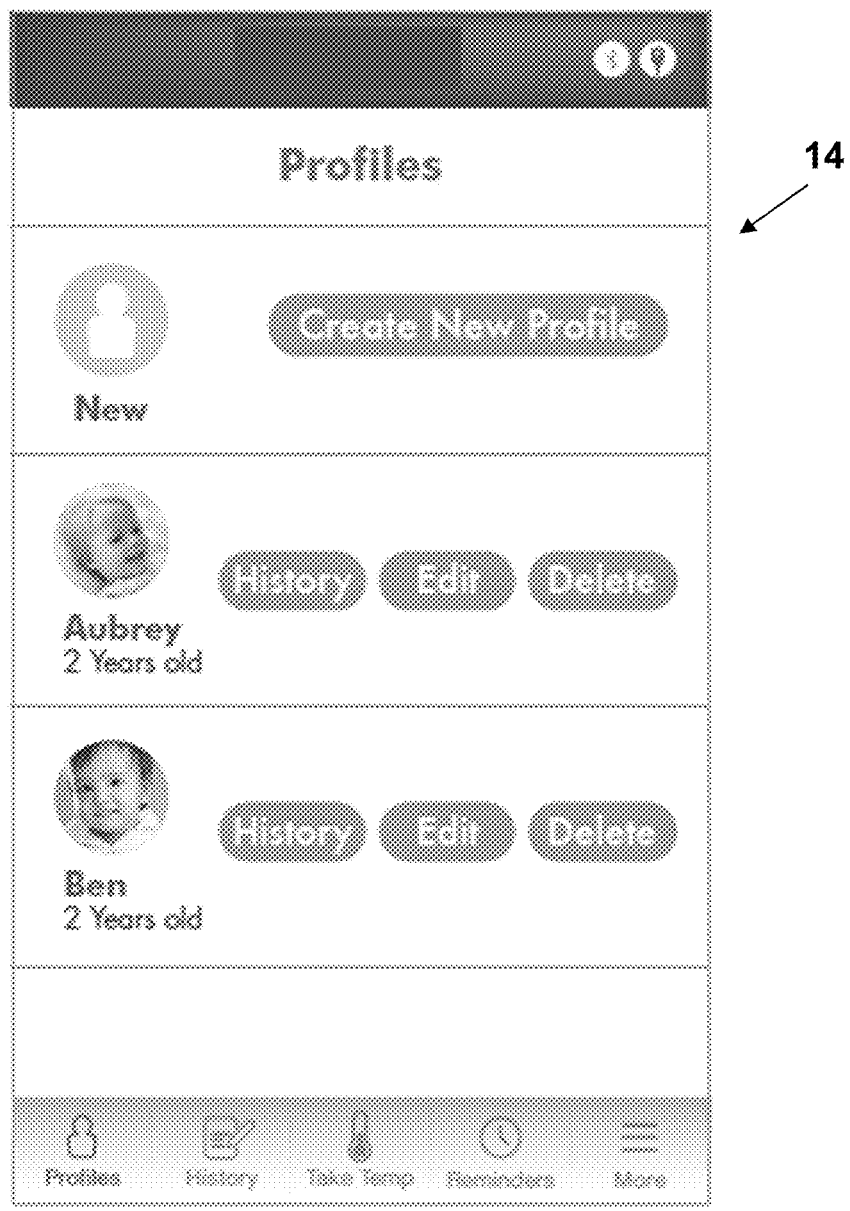
FIG. 5 illustrates another aspect of a user interface for the external computing device shown in FIG. 3.

The program in the computing device 10 may similarly provide the user interface 14 on display 12 to support management functions for the thermometer 100, such as setting a temperature mode (oral, tympanic, axillary, etc.), resetting the thermometer 100 to a default state, setting or overriding a measurement parameter (e.g.: degrees Celsius or Fahrenheit; setting the internal clock of the computation module 112; setting the temperature type; setting the patient indicator), assigning buttons 108 or button 108 positions to a patient or indicating by suitable signaling the specific patient that is being measured, and the results of these management functions selected by the user may then be transmitted to the thermometer 100, with the computation module 112 updating the configuration data 212 and adjusting its functionality accordingly. Hence, many, or all, user input/output functions can be offloaded onto the eternal computing device 10, thus reducing the number of components required, and the associated costs, of the thermometer 100. The user interface 14 may also be used to manage temperatures that have been taken by the thermometer 100 and stored into the external device 10, such as creating a patient profile (name, age, location, etc., as indicated in FIG. 5), assigning readings to a patient, deleting saved readings and the like. Relevant aspects of patient profile data, and in particular patient age, may be downloaded from the external device 10 to the thermometer 100, which the thermometer 100 may then use when computing temperatures or controlling certain functions of the thermometer.

In preferred embodiments, the user interface 14 of the external device 10 can set a color of the temperature presented on the screen 12, or a similar visual indicator, based upon the severity of the measured fever, if any—i.e., green for a normal temperature, yellow for an elevated temperature and red for a fevered condition, as described, for example, in U.S. Pat. No. 7,350,973, entitled "COLOR CHANGING THERMOMETER," the contents of which are incorporated herein by reference. More preferably, the temperature ranges associated with the specific colors used to indicate the temperature state on the display 12 may also be based on the age of the patient as determined from the patient indicator obtained either from the associated data 214 obtained from the thermometer 100 or as indicated subsequently by a user via the user interface 14 and associated with entered patient profile data 214. Such age-based calculations may be performed, for example, as disclosed in U.S. patent application Ser. No. 12/966,697, entitled "THERMOMETER WITH AGE SPECIFIC FEATURE SELECTION," the contents of which are incorporated herein by reference. The temperature ranges associated with the specific colors may also be based upon the location on the patient where the temperature was taken, such as oral, tympanic or the like. Preferably, the user interface 14 presents visual indicia on the screen 12 to indicate, together with the related temperature and color indicator, the type of temperature taken (oral, tympanic, etc.) and the age range of the patient (infant, child, adult, etc.). This indicia, could be, for example, a picture of an infant, a child, or an adult presented on the screen 12 based upon the age range of the patient, or a check box or the like next to text indicative of the age range, or any other suitable indicia. In alternative embodiments, the body 102 of thermometer 100 may include one or more LEDs or the like, controllable by the computation module 112, that illuminate based upon the age range. For example, a single illuminated LED could indicate an infant, two illuminated LEDs could indicate a child, etc.; or the LEDs could illuminate text on the body 102 that indicates the age range, or could illuminate to present a graphical indication of the age range.

The computation module 112 of the thermometer 100 may keep track of the last measurements 216 stored in its memory 206 that were recorded but never provided to the external device 10 and, when a new communications link 2 is established, transmit these most recent temperature measurements 216 and their related data to the external device 10. Hence, in response to establishing the communications link 2, the computation module 112 may scan its memory 206 for any temperature measurements 216 that have not been previously provided to the external device 10 and use the wireless module 114 to provide such measurements 216 to the external device 10. In this manner the thermometer 100 can "push" temperature readings to the external computing device 10. Such "pushed" measurements may then be deleted from the memory 206 of the thermometer 100, or may be tagged as downloaded, such as by associating an identifier of the external device 10 with the temperature entry data 216 that was "pushed" to device 10. Temperature data 216 that exceeds a certain date or time range may be automatically deleted from memory 206. Alternatively, the user interface 14 of the application on the external device 10 may allow a user to manage and delete temperature data 216 stored in the memory 206 of the thermometer 100. If the received measurements 216 do not contain any indicator of the patient, such as a patient ID, the external device 10 may present a prompt on display 12 to allow the user to input the respective patient identifiers. This temperature-related information can then be stored in the memory of the external device 10 for subsequent processing and display.

Preferably, when providing temperature measurements 216 to the external device 10, each temperature measurement 216 is also transmitted with its associated data, including, for example: (1) the date and time when the measurement was taken; (2) the type of temperature computed or determined, such as oral, rectal, axillary, tympanic, etc.; (3) a patient identifier (i.e., the position or state of the related patient indicator button or slider 108, the physical location of the thermometer 100, or a name/identifier earlier provided by the external device 10), and (4) any other related data, such as ambient temperature, raw sensor data or the like. The external device 10 can then display not only the numerical value of the temperature of the patient, but also when the temperature was taken, the type of temperature being displayed and the name (or an associated number, for example) of the patient. If raw sensor data is provided with the reading data 216, the application program may compute a converted temperature on its own and present such converted temperature on the display 12. The application program of the external device 10 may also keep track of a predetermined number of temperature readings, or request these from the thermometer 100, and display them on the display 12 so that the progress of the patient can be seen as a function of time. This plurality of temperature measurements can be presented on display 12, for example, in columnar form as a chart, or may be displayed more visually, such as a graph of temperature versus time.

In some embodiments the thermometer 100 can use the communications link 2 to send raw data obtained from the sensor assembly 120 to the computing device 10. This data may be continuously output at a predetermined frequency, such as 10 readings per second or the like, and include data related to one or more sensors present in the sensor assembly 120, such as an ambient temperature sensor and a target temperature sensor. The external computing device 10 can use this raw data to, for example, present raw temperature information from the sensor assembly 120 on the display 12, and/or to compute or determine and then display a converted patient temperature value, e.g., oral, rectal, axillary, tympanic, etc.

In some embodiments, the thermometer 100 may include one or more lighting devices controllable by the computation module 112 to provide one or more of an indicator that a temperature measurement is in progress, has been completed, and a condition of the measured temperature. For example, the lighting devices may include a single red LED and a single green LED, in which the red LED is illuminated when an abnormal temperature is detected, and the green LED is illuminated when a normal temperature is detected. One or both of these LEDs may blink, for example, to indicate that a temperature measurement is in progress. Alternatively, the lighting devices may include a plurality of lights, such as LEDs, that indicate the process of taking the patient's temperature; the lights may advance as the temperature is being taken, and when all lights are lit the user can then know that the temperature taking process is complete. Alternatively, the thermometer may include a vibrating mechanism and/or speaker that is activated when the temperature-taking process is starting, is complete, when the thermometer is ready for use, etc.

Those skilled in the art will recognize that the present invention has many applications, may be implemented in various manners and, as such is not to be limited by the foregoing embodiments and examples. Any number of the features of the different embodiments described herein may be combined into a single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there has been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art.

What is claimed is:

1. A thermometer system including a thermometer in combination with an application stored on an external device,
   the thermometer comprising:
   at least a sensor for obtaining a temperature reading from a patient and generating a corresponding sensor signal;
   a computation circuit coupled to the sensor and configured to receive the sensor signal and compute a corresponding temperature value; and
   a wireless communications circuit coupled to the computation circuit;
   wherein the wireless communications circuit and the computation circuit are collectively configured to establish a wireless communications link with the external device to provide the temperature value to the external device,
   the application stored on the external device configured to receive and store patient profile data associated with a patient profile and associate the temperature value with the patient profile stored on the external device, which is separate from the thermometer.

2. The thermometer system of claim 1 wherein the computation circuit is configured to collect a plurality of temperature readings from the sensor and use the wireless communications link to provide a corresponding plurality of temperature values to the external device.

3. The thermometer system of claim 2 wherein the plurality of temperature values are provided to the external device for real-time presentation on a display of the external device.

4. The thermometer system of claim 1 wherein the computation circuit comprises a memory and a processor, and the processor is configured to store the temperature value in the memory.

5. The thermometer system of claim 4, wherein the processor is configured to provide the temperature value stored in the memory to the external device via the communications link in response to establishment of the communications link.

6. The thermometer system of claim 5, wherein the processor is configured to identify the temperature value stored in the memory as provided to the external device, or to delete the temperature value from the memory, in response to having previously provided the temperature value to the external device.

7. The thermometer system of claim 4, wherein the computation circuit further comprises a clock and the processor is further configured to store a date, time or both provided by the clock in the memory corresponding to the temperature value.

8. The thermometer system of claim 7 wherein the processor is further configured to use the communications link to provide the date, time or both corresponding to the temperature value to the external device.

9. The thermometer system of claim 4, wherein the processor is configured to use the communications link to obtain configuration information from the external device and store the configuration information in the memory.

10. The thermometer system of claim 4 wherein the wireless communications circuit and the computation circuit are further collectively configured to estimate a position of the thermometer based upon one or more wireless signals.

11. The thermometer system of claim 10 wherein the computation circuit is further configured to associate the position of the thermometer with the patient.

12. The thermometer system of claim 4 wherein the computation circuit is further configured to store information about a plurality of patients and respective patient data in the memory.

13. The thermometer system of claim 12 further comprising an input device coupled to the computation circuit, and the computation circuit is further configured to select information about a particular patient from among the information about the plurality of patients stored in the memory.

14. The thermometer system of claim 12 wherein the wireless communications circuit and the computation circuit are further collectively configured to select information about a particular patient from among the information about the plurality of patients stored in the memory.

15. The thermometer system of claim 1 further comprising at least a lighting device controllable by the computation circuit to indicate one or more of an abnormal temperature, a normal temperature and a status of the thermometer.

16. The thermometer system of claim 15 wherein at least the lighting device comprises a red light emitting diode (LED) and a green LED, the green LED illuminating when a normal temperature is measured, and the red LED illuminating when an abnormal temperature is measured.

17. The thermometer system of claim 1 further comprising a lighting device controllable by the computation circuit to indicate a status of the temperature reading.

18. The thermometer system of claim 1 wherein the temperature value is a converted temperature value based upon the sensor signal.

19. The thermometer system of claim 1 wherein the temperature value is a raw temperature value obtained from sensor signal.

20. The thermometer system of claim 19 wherein the wireless communications circuit and the computation circuit are further collectively configured to provide additional raw data to the external device sufficient to permit the external device to compute a converted temperature value.

21. The thermometer system of claim 1 wherein the wireless communications circuit and the computation circuit are further collectively configured to receive the sensor signal, compute the corresponding temperature value and provide the temperature value to the external device in response to receiving a signal from the external device.

22. A method for providing a temperature value of a patient, the method comprising:
establishing a wireless communications link with a thermometer;
utilizing the wireless communications link to obtain at least a temperature reading from the thermometer;
associating the temperature value of the patient with a patient profile stored on a device separate from the thermometer; and
utilizing the temperature reading to present a corresponding temperature value and associated patient profile information on a display;
wherein the display is on the device separate from the thermometer.

23. The method of claim 22, wherein the temperature value is a raw value of the temperature reading.

24. The method of claim 22, wherein the temperature value is a converted temperature based upon the temperature reading.

25. The method of claim 24, therein the temperature reading obtained from the thermometer is the converted temperature.

26. The method of claim 24 further comprising utilizing the temperature reading to compute the converted temperature.

27. The method of claim 22, further comprising:
utilizing the wireless communications link to obtain a plurality of temperature readings from the thermometer; and
utilizing the temperature readings to present corresponding temperature values on the display to indicate progress of a temperature measuring process of the patient.

28. The method of claim 22, further comprising utilizing the wireless communications link to provide configuration information to the thermometer.

29. The method of claim 22 wherein the display is on a wireless communications device.

30. The method of claim 29 further comprising:
downloading a program into the wireless communications device, the program configured to be executed by the wireless communications device to establish the wireless communications link with the thermometer, and to present to corresponding temperature on the display.

31. A method for providing a temperature value of a patient, the method comprising:
using a sensor of a thermometer to obtain a temperature reading from the patient;
establishing a wireless communications link between the thermometer and an external device;
associating the temperature value of the patient with a patient profile stored on a device separate from the thermometer; and
utilizing the wireless communications link to provide at least the temperature reading to the external device so that the external device can present a corresponding temperature value and associated patient profile information on a display;
wherein the display is not on the thermometer.

32. A method for displaying a temperature of a patient, comprising:
establishing a wireless communication link with a thermometer;
receiving a plurality sensor signals from the thermometer;
utilizing the plurality of sensor signals to present, on a display, progress of a temperature-taking process performed by the thermometer;
associating the temperature of the patient with a patient profile stored on a device separate from the thermometer; and
presenting a converted temperature value of the patient and associated patient profile information on the display.

33. The method of claim 31, further comprising:
presenting, on the display, an option for a plurality of temperature modes;
accepting input from a user accepting one of the plurality of temperature modes; and
presenting the converted temperature value of the patient on the display according to a selected temperature mode.

34. The method of claim 31, further comprising providing the selected temperature mode to the thermometer.

35. The method of claim 31, further comprising obtaining the converted temperature value from the thermometer.

36. The method of claim 31, further comprising computing the converted temperature value based upon one or more of the sensor signals obtained from the thermometer.

* * * * *